United States Patent [19]

Faul et al.

[11] Patent Number: 5,665,877

[45] Date of Patent: Sep. 9, 1997

[54] SYNTHESIS OF BISINDOLYLMALEIMIDES

[75] Inventors: Margaret M. Faul, Zionsville; Michael R. Jirousek; Leonard L. Winneroski, II, both of Indianapolis, all of Ind.

[73] Assignee: Eli Lilly and Company, Indianapolis, Ind.

[21] Appl. No.: 650,922

[22] Filed: May 17, 1996

Related U.S. Application Data

[62] Division of Ser. No. 452,613, May 25, 1995, Pat. No. 5,614,647, which is a division of Ser. No. 317,140, Oct. 3, 1994, Pat. No. 5,541,347, which is a continuation-in-part of Ser. No. 163,060, Dec. 7, 1993, abandoned.

[51] Int. Cl.$^6$ .................................................. C07D 498/22
[52] U.S. Cl. .......................... 540/469; 548/416; 548/478; 552/1; 552/105; 556/444; 558/46; 558/47; 560/111; 560/160; 560/266; 564/92; 564/93; 564/98; 564/99; 564/183; 564/224; 564/462; 564/508
[58] Field of Search .................. 540/469; 548/416, 548/478; 552/1, 105; 556/444; 558/46, 47; 560/111, 160, 266; 564/92, 93, 98, 99, 183, 224, 462, 508; 568/660

[56] References Cited

U.S. PATENT DOCUMENTS

| | | | |
|---|---|---|---|
| 4,923,986 | 5/1990 | Murakata et al. | 540/545 |
| 5,057,614 | 10/1991 | Davis et al. | 548/466 |
| 5,438,050 | 8/1995 | Kleinschroth et al. | 514/183 |

FOREIGN PATENT DOCUMENTS

| | | |
|---|---|---|
| 3914764 A1 | 11/1990 | Denmark. |
| 0 434 057 A2 | 12/1990 | Denmark. |
| 0 269 025 A2 | 11/1987 | European Pat. Off.. |
| 0 470 490 A1 | 7/1991 | European Pat. Off.. |
| 0 540 956 A1 | 10/1992 | European Pat. Off.. |
| 0 328 000 A2 | 2/1989 | Germany. |
| 0 384 349 A1 | 2/1990 | Germany. |
| 0 397 060 A2 | 5/1990 | Germany. |
| WO 91/13071 | 9/1991 | WIPO. |
| WO91/13070 | 9/1991 | WIPO. |
| WO94/02488 | 2/1994 | WIPO. |
| WO94/07895 | 4/1994 | WIPO. |

OTHER PUBLICATIONS

Derwent Abstract 90–132947/18; 21.10.88–DE–835842 (1988).
Derwent Abstract 92–274042/33;90.11.20 90JP–314628 (1990).
Meier, et al., *Tetrahedron Letters*, 34:33, 5277–5280 (1993).
Wilkinson, et al., *Bichem. J.*, 294, 335–337 (1993).
Bit, et al., *J. Med. Chem.*, 36, 21–29 (1993).
Martiny–Baron, et al., *The Journal of Biological Chemistry*, 268:13, 9194–9197 (1993).
Krakowiak, et al, *Synlett*, 611–620, (Sep. 1993).
Mulqueen, et al., *Agents Actions*, 37, 85–89 (1992).
Davis, et al., *J. Med. Chem.*, 35, 177–184 (1992).
Davis, et al., *J. Med. Chem.*, 35, 994–1001 (1992).

Toullec, et al., *The Journal of Biological Chemistry*, 266:24, 15771–15781 (1991).
Nixon, et al., *Drugs Exptl. Clin. Res.*, 17:8, 389–393 (1991).
Davis, et al., *Tetrahedron Letters*, 31:36, 5201–5204 (1990).
Brenner, et al., *Tetrahedron Letters*, 44:10, 2887–2892 (1988).
Joyce, et al., *The Journal of Organic Chemistry*, 52: 7, 1177–1186 (1987).
Buchdunger, et al., *Proc. Natl. Acad. Sci. USA*, 91, 2334–2338 (Mar. 1994).
Kobayashi, et al., *The American Physiological Society*, H1214–H1220 (1994).
Felsenstein, et al., *Neuroscience Letters*, 174 173–176 (1994).
Demaerschalck, et al., *Biochimica et Biophysica Acta*, 1181 214–218 (1993).
Shimohama, et al., *Neurology*, 43 1407–1413 (1993).
Ansell, et al., *Journal of Chemical Society*, 1788–1795 (1957).
Rudloff, et al., *Canadian Journal of Chemistry*, 35 315–321 (1957).
Tius, et al., *J. Am. Chem. Soc.*, 108 1035–1039 (1986).
Gillet, et al., *Synthesis*, 355–360, (May 1986).
DeCamp Schuda, et al., *Synthesis*, 309–312, (Apr. 1986).
Kaneko, et al., *Tetrahedron Letters*, 26, 4015–4017 (1985).
Edge, et al., *Chemistry & Industry*, 18:130, (Feb. 1991).
Steglich, et al., *Angew: Chem. Int. Ed. Engl.*, 19: (6): 459–460 (1980).
Harris, et al., *Tetrahedron Letters*, 34 (51): 8361–8364 (1993).

(List continued on next page.)

*Primary Examiner*—Richard L. Raymond
*Attorney, Agent, or Firm*—Steven P. Caltrider; David E. Boone; Ronald S. Maciak

[57] ABSTRACT

The present invention provides a novel synthesis of the compounds of Formula (I):

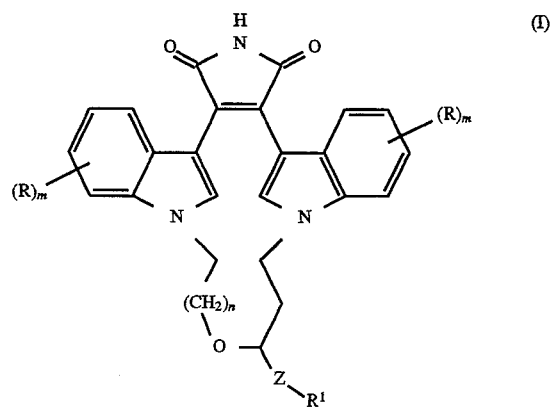

The compounds are produced in high yield and without utilizing expensive chromatographic separations. The synthesis is particularly advantageous because it is stereoselective.

6 Claims, No Drawings

OTHER PUBLICATIONS

Bergman, et al., *Tetrahedron Letters*, 28: (38): 4441–4444 (1987).
Behling, et al., *Tetrahedron Letters*, 30: (1): 27–30 (1989).
Alexakis, et al., *Tetrahedron Letters*, 45: (19): 6179–6202 (1989).
Lipshutz, et al., *Tetrahedron Letters*, 29: (8): 893–896 (1988).
Fieser and Fieser, *Reagents for Organic Synthesis, XII*, John Wiley & Sons, p. 108 (1986).

Rudloff, et al., "Hydrogenation of Carbohydrates", *Canadian Journal of Chemistry*, 35, 315–321 (1957).

Rosenthal, et al., "The reaction of unsaturated carbohydrates with carbon monoxide and hydrogen. III. Structure and stereochemistry of the hexitols from 3,4–di–O–acetyl–d–arabinal", *Canadian Journal of Chemistry*, 42, 2025–2027 (1964).

SYNTHESIS OF BISINDOLYLMALEIMIDES

This application is a division of application Ser. No. 08/452,613 filed May 25, 1995, now U.S. Pat. No. 5,614,647 which is a division of application Ser. No. 08/317,140, now U.S. Pat. No. 5,541,347, filed Oct. 3, 1994 which is a continuation-in-part of Heath, et al., U.S. Ser. No. 08/163,060, filed Dec. 7, 1993, now abandoned.

BACKGROUND OF THE INVENTION

Therapeutically, an antagonist which possesses both kinase selectivity for protein kinase C (PKC) and PKC isozyme Selectivity is a potentially useful pharmacological agent. Hartenstein, J. H., et al., in "perspectives in Medicinal Chemistry," 99–118 (1993), VCH Publishers, New York. Such an antagonist of protein kinase C would be useful in treating disease states in which PKC has been implicated. Lester, D. S., et al., "Protein Kinase C: Current concepts and Future Perspectives", Ellis Horwood New York (1992). Specific isozymes of protein kinase C have been implicated in cancer (Ahmed, et al., *Mol, Pharma.*, 43, 858–86 (1993), CNS diseases such as Alzheimer's; Demaerschalck, et al., *Biochem. Biophys. Acta.* 1181, 214–218 (1993), cardiovascular disease; (Natarajan et al. *Mol. Cell. Endo.*, 101, 59–66 (1994)) and diabetic complications; King, et al., *Proc. Nat. Acad. Sciences (USA)*, 88:22, 11059–63 (1992).

Recently, bisindolylmalimides of the formula:

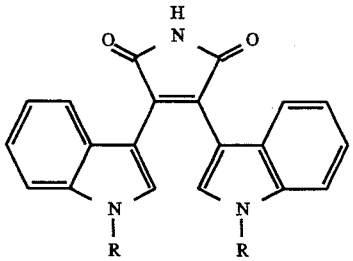

have been recognized as PKC selective agents and have shown promise as therapeutic agents for treating diseases implicated by PKC. Bit, et al., *J. Med. Chem*, 56:21 (1993). Wikinson S. E., et al., *Biochem J.*, 299, 335 (1993). Toullec, D., et al., *J. Biol. Chem.*, 266, 15771 (1991); Davis, P. D., et al., *J. Med. Chem.*, 35, 177 (1992).

U.S. patent application Ser. No. 08/163,060 discloses a novel class of compounds that are potent and effective inhibitors of PKC. These compounds are of the Formula (I):

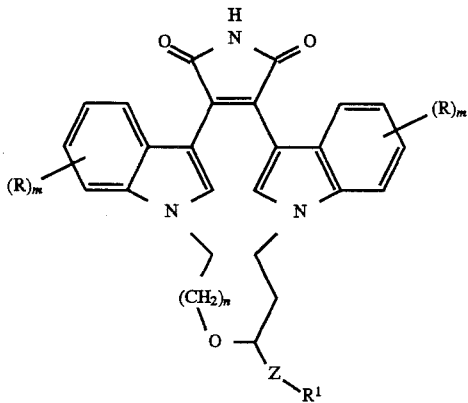

and are prepared by coupling a bisindolylmaleimide with a linker of the Formula (II):

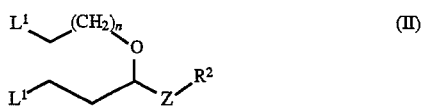

to form the N to N linked bisindolylmaleimide.

The present invention provides novel compounds of the Formula (II) and the stereoselective synthesis of these compounds. Under the preferred conditions, the compounds are produced in high yield and without utilizing expensive chromatographic separations. The synthesis is particularly advantageous because it further provides a stereoselective route of preparing the compounds of the Formula (I).

SUMMARY OF THE INVENTION

The invention provides Compounds of the Formula:

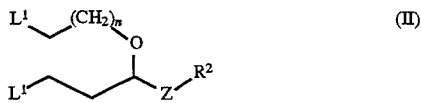

wherein:

$R^2$ is $N_3$, NH-protecting group, amine protecting group, or hydroxy protecting group;

$L^1$ is independently a leaving group;

Z is $-(CH_2)_n-$; and n is independently 1, 2, or 3.

The invention further provides a stereoselective process of preparing these compounds, which comprises:

(a) Alkylating a compound of Formula (III):

with a lithium acetylide, a cerium acetylide, or a vinyl organometalic reagent selected from vinyl cuprate, vinyl aluminum, vinyl tin, vinyl lithium, or vinyl Grignard;

to produce a compound of the Formula (IV):

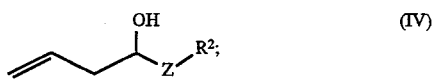

(b) reacting a compound of the Formula (IV) with a compound of the Formula:

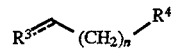

wherein $R^3$ is halo, a protected hydroxy, or combines with the adjacent carbon to form an olefin; $R^4$ is chloro, bromo, or iodo;

to form a compound of the Formula (V)

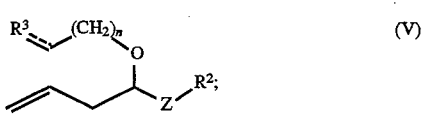

(c) converting the compound of the Formula (V) to a compound of the Formula (II).

Compound (II) is useful in the preparation of the compounds of the Formula (I), which are potent PKC inhibitors.

DETAILED DESCRIPTION AND PREFERRED EMBODIMENTS

As noted above, the invention provides a novel synthesis for the preparation of a compound of the Formula (II):

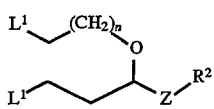

Particularly preferred compounds of the Formula II are when $L^1$ and $L^1$ are the same and are mesyl or iodo; n is 1; and $R^2$ is —O-trityl or —O-mono- or di-methoxytrityl.

Compound II is useful for the preparation of compounds of Formula I:

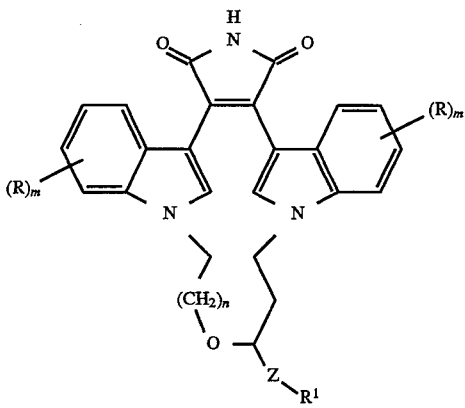

wherein:

Z is —(CH$_2$)$_n$—;

R is independently hydrogen, halo, C$_1$-C$_4$ alkyl, hydroxy, C$_1$-C$_4$ alkoxy, haloalkyl, nitro, NR$^5$R$^6$, or —NHCO (C$_1$-C$_4$ alkyl );

$R^1$ is C$_1$-C$_4$ alkyl, C$_1$-C$_4$ alkoxy, (CH$_2$)$_m$aryl, (CH$_2$)$_m$aryloxy, hydroxy, carboxy, —COO(C$_1$-C$_4$ alkyl)), —COO((CH$_2$)$_m$aryl), —CO(C$_1$-C$_4$ alkyl), —NR$^5$R$^6$, —(NR$^5$R$^6$)(OR$^5$), —NH(CH$_2$)$_m$aryl, —NH (CH$_2$)$_m$pyridyl, —CONH((CH$_2$)$_m$aryl ), —CONH (C$_1$-C$_4$ alkyl), —NHCO(C$_1$-C$_4$alkyl), —NHCO(CH$_2$)$_m$aryl, —OCONH(C$_1$-C$_4$ alkyl), —OCONH(CH$_2$)$_m$aryl, —NHCOO(alkyl), —NHCOO (benzyl), —NHSO$_2$(C$_1$-C$_4$ alkyl), —NHSO$_2$(CH$_2$)$_m$aryl, —CN, —SH, —S(C$_1$-C$_4$ alkyl), —S(aryl), —SO$_2$(NR$^5$R$^6$), —SO$_2$(C$_1$-C$_4$ alkyl), or —SO(C$_1$-C$_4$ alkyl);

$R^5$ and $R^6$ are independently hydrogen, methyl, phenyl, benzyl, or combine to the nitrogen to which they are bonded to form a saturated or unsaturated 5 or 6 membered ring; and m is independently 0, 1, 2 or 3.

The most preferred compounds of the Formula I are those wherein R is hydrogen; $R^1$ is NR$^5$R$^6$; n is 1; m is 1; and $R^5$ and $R^6$ are methyl.

Compounds of the Formula I are disclosed in U.S. patent application Ser. No. 08/163,060. As PKC inhibitors, the compounds are useful for treating conditions that protein kinase C has demonstrated a role in the pathology, such as ischemia, inflammation, central nervous system disorders, cardiovascular disease, dermatological disease, cancer and, in particular, diabetes mellitus.

The term "halo", as used herein, represents fluorine, chlorine, bromine, or iodine.

The term "C$_1$-C$_4$ alkyl" represents a cyclo, straight or branched chain alkyl group having from one to four carbon atoms such as methyl, ethyl, n-propyl, isopropyl, cyclopropyl, n-butyl, isobutyl, sec-butyl, t-butyl and the like. A haloalkyl is one such alkyl substituted with one or more halo atoms, preferably one to three halo atoms. An example of a haloalkyl is trifluoromethyl. A C$_1$-C$_4$ alkoxy is a C$_1$-C$_4$ alkyl group covalently bonded by an —O— linkage.

The term "aryl" represents a substituted or unsubstituted phenyl or naphthyl. Aryl may be optionally substituted with one or two groups independently selected from hydroxy, carboxy, C$_1$-C$_4$ alkoxy, C$_1$-C$_4$ alkyl, haloalkyl, nitro, —NR$^5$R$^6$, —NHCO(C$_1$-C$_4$ alkyl), —NHCO(benzyl), —NHCO(phenyl), SH, S(C$_1$-C$_4$ alkyl), —OCO(C$_1$-C$_4$ alkyl), —SO$_2$(NR$^5$R$^6$), —SO$_2$(C$_1$-C$_4$ alkyl), —SO$_2$ (phenyl), or halo. The term aryloxy is one such aryl covalently bonded by an —O— linkage. The term (CH$_2$)$_m$aryl is preferably benzyl or phenyl.

The term "leaving group" as used in the specification is understood by those skilled in the art. Generally, a leaving group is any group or atom that enhances the electrophilicity of the atom to which it is attached for displacement. Preferred leaving groups are triflate, mesylate, tosylate, imidate, chloride, bromide, and iodide.

The term "hydroxy protecting group" as used in the specification refers to one of the ether or ester derivatives of the hydroxy group commonly employed to block or protect the hydroxy group while reactions are carried out on other functional groups on the compound. The species of hydroxy protecting group employed is not critical so long as the derivatized hydroxy group is stable to the condition of subsequent reaction(s) and can be removed at the appropriate point without disrupting the remainder of the molecule. T. W. Greene and P. Wuts, *Protective Groups in Organic Synthesis*, John Wiley and Sons, New York, N.Y., 1991, provide a list of commonly employed protecting groups. Preferred hydroxy protecting groups are tert-butyldiphenylsilyloxy (TBDPS), tert-butyldimethylsilyloxy (TBDMS), triphenylmethyl (trityl, mono- or di-methoxytrityl, or an alkyl or aryl ester. A related term is "protect hydroxy," which refers to a hydroxy group substituted with a hydroxy projecting group.

The term "amino protecting group" as used in the specification refers to substituents of the amino group commonly employed to block or protect the amino functionality while reacting other functional groups on the compound. The species of amino-protecting group employed is not critical so long as the derivatized amino group is stable to the condition of subsequent reaction(s) and can be removed at the appropriate point without disrupting the remainder of the molecule. T. W. Greene and P. Wuts, *Protective Groups in Organic Synthesis*, Chapter 7, provide a list of commonly employed protecting groups. See also J. W. Barton, *Protective Groups in Organic Chemistry*, Chapter 2. Preferred amino-protecting groups are t-butoxycarbonyl, phthalimide, an —NH cyclic alkyl, and benzyloxycarbonyl. The related term "protected amino" defines an amino group substituted with an amino protecting group as previously defined.

The term "—NH protecting groups" as used in the specification refers to sub-class of amino protecting groups that are commonly employed to block or protect the —NH functionality while reacting other functional groups on the compound. The species of protecting group employed is not critical so long as the derivatized amino group is stable to the condition of subsequent reaction(s) and can be removed at the appropriate point without disrupting the remainder of the molecule. T. W. Greene and P. Wuts, *Protective Groups in Organic Synthesis*, Chapter 7, page 362-385, provide a list of commonly employed protecting groups. Preferred —NH protecting groups are carbamate, amide, alkyl or aryl sulfonamide. The related term "protected —NH" defines an —NH group substituted with an —NH protecting group as defined.

The synthesis of the macrocycles of Formula I is carried out as follows:

Scheme 1

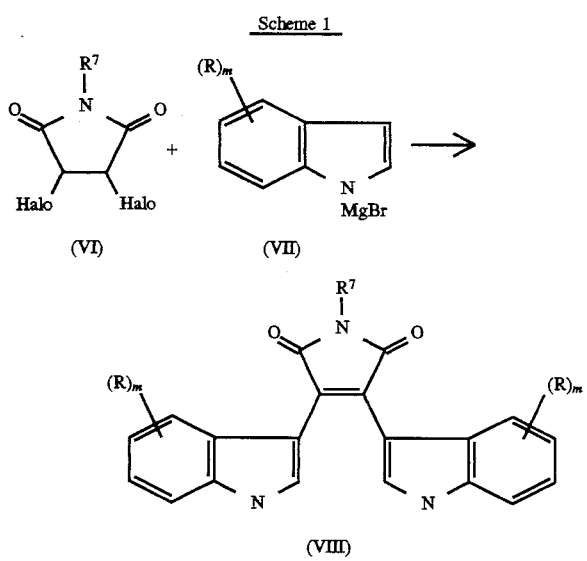

(VI)  (VII)

(VIII)

In the above scheme, $R^7$ is methyl or hydrogen. R and m are the same as previously defined. The reaction illustrated in Scheme 1 is often referred to as a Grignard reaction. The reaction is generally described by Brenner, et al., Tetrahedron, 44, 2887–2892 (1988). Generally, the reaction of Scheme 1 is carried out in an inert solvent such as benzene, toluene, tetrahydrofuran or ether at a temperature between room temperature and reflux temperature of the reaction mixture. Compound (VII) is preferably prepared in situ from the indole and an alkyl magnesium halide such as ethyl magnesium bromide or ethyl magnesium iodide in a manner known in the art.

Most significantly, the reaction depicted in Scheme 1 is dependent on solvent conditions. When carried out in a Toluene:THF:ether solvent system the reaction of Scheme 1 provides Compound VIII in greater than 80 percent yield and greater than 95 percent purity. The product is precipitated from the reaction mixture with ammonium chloride, $NH_4Cl$.

The linker portion of the macrocycles of Formula (I) is prepared in accordance with Scheme 2.

Scheme 2

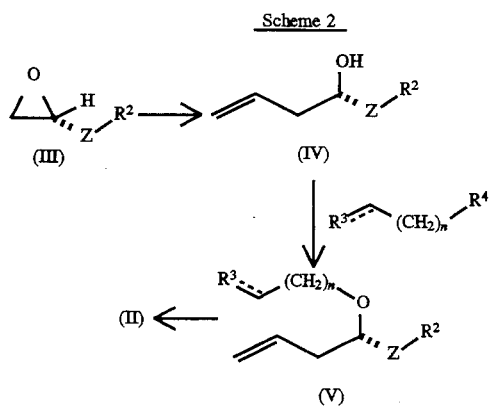

Z, $R^2$, $R^3$, $R^4$, and n are the same as previously defined. Scheme 2 presents a stereoselective synthesis of the linker portion of the macrocycle. The S-enantiomer is illustrated above; however, one skilled in the art would recognize that the complimentary enantiomer, or a mixture of enantiomers could be prepared in an analogous manner.

The regioselective opening of epoxide, Compound (III), is carried out by alkylating a compound of Formula (III):

(III)

with a lithium acetylide, a cerium acetylide, or organometalic reagent selected from vinyl cuprate, vinyl aluminum, vinyl tin, vinyl lithium, or vinyl Grignard. Preferably, a vinyl organometalic reagent is a compound of the formula: vinyl MgBr, vinyl MgCl, vinyl Li, vinyl(thienyl)Cu(CN)$Li_2$, Vinyl(thienyl)Cu(CN)LiMgBr, or a lithium acetlyene:EDTA complex.

The reaction between the epoxide (III) and the organometalic occurs under conditions appreciated in the art. The reaction between a vinyl Grignard and an epoxide in the presence of a catalytic cuprate is described in Tius M. A., et al., J. Am. Chem. Soc. 108(5): 1035–1039 (1986) and DeCampshuda A. et al. Synthesis-Stuttgart (4), 309–312 (1986). Likewise, Gillet J. P. et al., Synthesis-Stuttgart (5), 355–360 (1986) describe the use of a vinyl lithium reagent in the presence of a lewis acid to open the epoxide; Lipshutz B. H., et al., Tetrahedron Lett. 29(8): 893–896 (1988) disclose higher order cuprates to open vinyl epoxides; Behling J. R., Tetrahedron Lett. 30(1): 27–30 (1989) disclose stannyl or vinyl tin reagents useful to open the epoxide; Alexakis A., et al., Tetrahedron 45(19): 6197–6202 (1989) disclose the use of a vinyl aluminate to open the epoxide; and the lithium acetylide reduction of the epoxide is disclosed in Synthesis, 139–141 (1987). When carried out with lithium acetylide or a cerium acetylide, an additional reduction with $H_2$/Lindlar's catalyst is necessary to produce the allyl, Compound IV.

Preferably, the reaction is carried out with vinyl MgBr or MgCl in the presence of a catalytic cuprate such as CuI or CuBr. The reaction is carried out in an inert solvent at a temperature between about –80° C. to the reflux temperature of the reaction mixture; preferably the temperature is –20° C. to 30° C. The reaction produces Compound (IV) which may be further reacted without purification.

Compound IV is alkylated or allylated under conditions appreciated in the art for coupling an alcohol to a alkyl or allyl halide to form the ether, Compound (V):

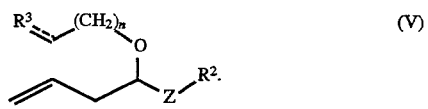

(V)

The reaction is commonly known as the Williamson Synthesis. The reaction involves a nucleophilic substitution of an alkoxide ion with the halide ion ($R^4$). The alkoxide ion is preferably generated in the presence of a base such as NaOH, KOH, or NaH in an aprotic solvent such as DMSO, THF, DMF, ether, or toluene.

Compound (V) is converted to Compound (II) by techniques appreciated in the art. For example, when $R^3$ is an olefin such as =$CR^8R^9$ wherein $R^8$ and $R^9$ are independently hydrogen, aryl, or $C_1$–$C_4$ alkyl, Compound (V) is converted to an ozonide by treating with ozone at low temperatures. The ozonide is then reduced with $NaBH_4$, $LiAlH_4$, $BH_3$ or catalytic hydrogenation with excess $H_2$ to produce a hydroxy moiety. The hydroxy may be readily converted to leaving group $L^1$. For example, the mesyl leaving group is prepared by reacting the hydroxy with methanesulfonyl chloride in triethylamine. Alternatively, the free hydroxy is converted to a iodide or bromide leaving group using, for example, $CBr_4$ in triphenylphosphine.

One skilled in the art would recognize that the reaction of Scheme 2 is particularly advantageous when $R^3$ is $=CH_2$. Both double bonds may be converted to the ozonide and reduced simultaneously to produce a diol, which is readily converted to Compound (II) wherein both $L^1$ moieties are the same leaving group.

The preparation of Compound (II) in a manner described is an advantageous means of preparing Compound (II) in high yield. The process is efficient and suitable for large scale. The synthesis is particularly advantageous when $R^2$ is a protected hydroxy, specifically O-trityl. When $R^2$ is O-trityl, Compound II may crystallized from the reaction mixture thus avoiding expensive chromatographic steps. When $R^2$ is TBDPS or other protecting group, crystallization and purification are more difficult and expensive. The ability to produce a crystalline compound in high yield and purity without expensive chromatographic steps is clearly advantageous over other means of synthesizing Compound (II).

Compound (II) is coupled to Compound (VIII) as described in Scheme 3.

Scheme 3

II + VIII ——>

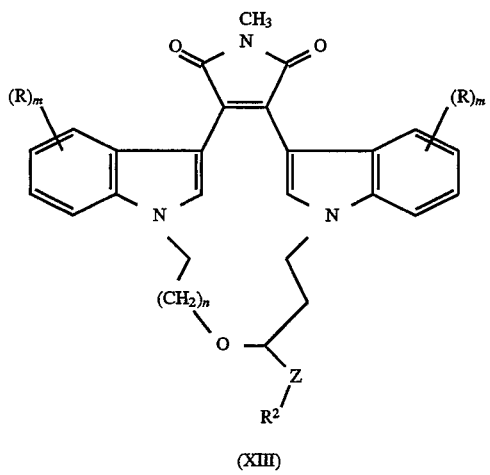

(XIII)

The reaction represented by Scheme 3 is accomplished by any of the known methods of preparing N-substituted indoles. This reaction usually involves approximately equimolar amounts of the two reagents, although other ratios, especially those wherein the alkylating reagent is in excess, are operative. The reaction is best carried out in a polar aprotic solvent employing an alkali metal salt or other such alkylation conditions as are appreciated in the art. When the leaving group is bromo or chloro, a catalytic amount of iodide salt, such as potassium iodide may be added to speed the reaction. Reaction conditions include the following: Potassium hexethyldisilazide in dimethylformamide or tetrahydrofuran, sodium hydride in dimethylformamide.

Preferably, the reaction is carried out under slow reverse addition with cesium carbonate in either acetonitrile, dimethylformide (DMF), or tetrahyofuran (THF). Slow reverse addition involves containing a mixture of Compound (VIII) and alkylating agent (II) with the base at a rate from about 0.1 mL/hour to about 2.0 ml/hour. The concentration of each reagent in the mixture is about 1.5 molar to about 0.001 molar. The slow addition results in a concentration of reagents in the reaction vessel of about 0.01 μmolar to 1.5 molar. One skilled in the art would recognize that at a higher rate of addition a lower concentration of reagents could be used in the reaction. Likewise, at a slower rate of addition, a higher concentration of reagents could be used in the reaction. Preferably, the compound is added at about 0.14 mL/hour with the compound and the alkylating agent at 0.37 molar. It is preferred that the $Cs_2CO_3$ be added in excess—most preferably a 4:1 ratio $Cs_2CO_3$ to alkylating agent. Preferred polar aprotic solvents are acetonitrile, dimethylformamide (DMF), acetone, dimethylsulfoxide (DMSO), dioxane, diethylene glycol methyl ether (diglyme), tetrahydrofuran (THF), or other polar aprotic solvents in which the reagents are soluble. The reaction is carried out at temperatures ranging from about 0° C. to reflux.

One skilled in the art would recognize that the ratio of the mixture of the compound and alkylating agent is not critical. However, it is preferred that the reagents are mixed in a ratio of 0.5 to 3 equivalents of each other. Most preferably, the reagents are mixed 1:1. The concentration of compound in the dissolving solvent is from saturation to about 0.01M.

Compound (XIII) is converted to the compound of the Formula I through the corresponding anhydride by an alkaline hydrolysis known in the art. Alkaline hydrolysis involves reacting the Compound (XIII) with a base, such as sodium hydroxide or potassium hydroxide, in $C_1$–$C_4$ alcohol (preferably ethanol), DMSO/water, dioxane/water, or acetonitrile/water at a temperature ranging from about 25° C. to preferably about reflux. The concentration of the reactants is not critical.

The anhydride is converted to the maleimide of Formula I by ammonolysis. Ammonolysis involves reacting the anhydride with an excess of hexamethyldisilazane or an ammonium salt (ammonium acetate, bromide, or chloride) and $C_1$–$C_4$ alcohol (preferably methanol) in an polar aprotic solvent such as DMF at room temperature. Preferably, the hexamethyldisilazane or an ammonium salt is reacted at a ratio greater than about 5:1 equivalents of anhydride.

The conversion of $R^2$ to the desired $R^1$ moiety is carried out by techniques known in the art for deprotecting an amine or hydroxy. For example, when $R^2$ is —O-trityl, the compound is de-tritylated with HCl gas in methylene chloride. The resulting hydroxy or amine may then be converted to the various substitutions of $R^1$ under standard conditions. For example, when $R^2$ is hydroxy, $R^2$ is converted to the mesylate with $MS_2O$ and pyridine in THF and subsequently converted to the dimethylamine or other amine substitution.

As previously stated, the present process is useful in preparing compounds of the Formula I. The compounds of the Formula I are PKC inhibitors and useful in treating diseases implicated by PKC. The compounds of Formula I inhibit PKC with an $IC_{50}$ of below 100 μm. In addition, the compounds selectively inhibit the beta-1 and beta-2 PKC isozymes and have an $IC_{50}$ value with respect to these isozymes of below 10 μm. The amount of compound administered is an amount that is capable of inhibiting PKC activity in mammals. The particular dose of the compound administered according to this invention will, of course, be determined by the particular circumstances surrounding the case, including the compound administered, the route of administration, the particular condition being treated, and similar considerations. The compounds of Formula I can be administered by a variety of routes including the oral, rectal, transdermal, subcutaneous, topical, intravenous, intramuscular or intranasal routes. For all indications, a typical daily dose will contain from about 0.01 mg/kg to about 20 mg/kg of the active compound of this invention. Preferred daily doses will be about 0.05 to about 10 mg/kg, ideally about 0.1 to about 5 mg/kg. However, for topical administration a typical dosage is about 1 to about 500 μg compound per cm² of an affected tissue. Preferably, the applied amount of compound will range from about 30 to about 300 µg/cm$^2$, more preferably, from about 50 to about 200 µg/cm$^2$, and, most preferably, from about 60 to about 100 µg/cm$^2$.

The following examples and preparations are provided merely to further illustrate the invention. The scope of the invention is not construed as merely consisting of the following examples. In the following examples and preparations, melting point, nuclear magnetic resonance spectra, mass spectra, high pressure liquid chromatography over silica gel, N,N-dimethylformamide, palladium on charcoal, tetrahydrofuran, and ethyl acetate are abbreviated M.Pt., NMR, MS, HPLC, DMF, Pd/C, THF, and EtOAc respectively. The terms "NMR" and "MS" indicate that the spectrum was consistent with the desired structure.

PREPARATION 1

Dichloro-N-methylmaleimide

A 3 L-three-necked flask fitted with a magnetic stir bar, digital thermocouple/thermometer, nitrogen purge and solid addition funnel was charged with 450 g (269.5 mol) of dichloromaleic anhydride; 191 g (282.8 mol) of methylamine hydrochloride and 1.6 L of acetic acid. The reaction mixture was then cooled to 10° C., and 160 g NaOMe added from the solid addition funnel over 1 hour while keeping the temperature between 10°–12° C. The reaction was allowed to stir at room temperature for 42 hours (24 hours is sufficient) then heated to 100° C. for 3 hours. HPLC analysis at this time indicated that all the starting material had disappeared. The reaction was cooled to room temperature and 2 L water was added. The mixture was then cooled to 3°–10° C. for 1 hour and filtered at 4° C. The solids were then rinsed with 2 L of cold deionized water. The pale yellow solid dried in an air oven overnight to afford 360 g (75%) yield of the titled compound 316726.

PREPARATION 2

(S)-Trityl Glycidol

Trityl chloride (2866 g, 10.3 mole) was dissolved in 7 L of CH$_2$Cl$_2$ under N$_2$. Triethylamine (1189 g, 1638 mL, 11.8 mole) was added, and then (R)-(–)-glycidol 329791(795.0 g, 10.6 mole) was added using 1 L of CH$_2$Cl$_2$ as a rinse. The reaction solution was heated to a gentle reflux (42° C.) for 3–4 hours. The reaction was cooled to room temperature and then 3 L of brine was added. The organic layer was dried (600 g Na$_2$SO$_4$) and evaporated in vacuo to give the titled compound as an oil that was recrystallized from ethanol to give 2354 g (70%) of the titled compound as a solid.

PREPARATION 3

2,3-Bis-(1H-indol-3-yl)-N-methylmaleimide

Indole (157.4 g, 1.343 mol, 2.2 eq.), toluene (2.28 L), and THF (412 mL) were charged to a 12 L reaction flask equipped with mechanical stirrer, thermocouple/Hastelloy probe, temperature controller, heating mantle, condenser, 500 mL addition funnel, and nitrogen inlet. The colorless solution was stirred briefly at ambient temperature under nitrogen.

3.0M EtMgBr solution in Et$_2$O (452 mL, 1.36 mol, 2.2 eq.) was charged to the addition funnel and added dropwise over 30 minutes to the indole solution, during which time an exotherm to 53° C. was observed. The pale green solution was heated to 60° C. and held there for 1 hour.

A solution of dichloro-N-methylmaleimide (110.0 g, 0.611 mol, 1.0 eq.) in toluene (578) mL was prepared and added streamwise to the reaction mixture over 5–10 minutes, during which time an exotherm to 67° C. and a dark heterogeneous mixture resulted. The mixture was heated to a gentle reflux (88° C.) and held there overnight until completed by HPLC.

The reaction mixture was cooled to 20°–30° C. Saturated ammonium chloride solution (1.76 L) was added, dropwise initially, until the exotherm to 35°–40° C. subsided, at which point the dark heterogeneous mixture converted to a red slurry. The slurry was stirred at 25°–30° C. for 2–4 hours. The product was isolated by filtration, rinsed with water and toluene, then dried in a vacuum oven at 50° C. 168 grams (80%) of product was obtained.

PREPARATION 4

1-(tert-butyldimethylsilyloxy)-4-(tert-butyldiphenylsilyloxy)-butan-2-ol

To an anhydrous CH$_2$Cl$_2$ (110 mL) solution of 3-buten-1-ol (15 g, 0.21 mol) was added imidazole (28.6 g, 0.42 mol, 2 eq), followed by tert-butyldimethylsilyl chloride (32 g, 0.22 mol). After 90 minutes, the reaction was complete as indicated by TLC (10% EtOAc/hexane). The CH$_2$Cl$_2$ solution was transferred to a separatory funnel, diluted with CH$_2$Cl$_2$ (110 mL), washed with water (200 mL), and brine (200 mL). The organic layer was collected, dried over MgSO$_4$, and filtered. The solvent was removed to yield an oil (1-(O-TBDMS)-3-butene) which was taken on to the next reaction. MS The above oil was dissolved in a mixture of acetone (400 mL) and water (50 mL). N-Methylmorpholine-N-oxide (85.2 g, 0.63 mol, 3 eq) was then added. The resulting slurry was cooled to 0° C., and after 10 minutes a catalytic amount of OsO$_4$ (0.3 g) was added. The resulting slurry was allowed to stir overnight, gradually warming to room temperature. TLC (25% EtOAc/hexane) indicated the reaction was complete. The reaction mixture was quenched with sodium bisulfite, diluted with ether (1 L), washed with water (400 mL), and brine (400 mL). The organic layer was collected. The aqueous layer extracted with ether (2×500 mL). The combined organic layers were dried, filtered, and concentrated to yield 4-(O-TBDMS)-1,2-butanediol as an oil, which was taken on to the next reaction.

The above oil was dissolved in anhydrous CH$_2$Cl$_2$ (250 mL). Imidazole (30 g, 0.44 mol, 2.5 eq) was added to the solution as a solid with stirring. The resulting solution was cooled to 0° C. After cooling 15 minutes, a CH$_2$Cl$_2$ (50 mL) solution of tert-butyldiphenylsilyl chloride (50 g, 0.18 mol, 1 eq) was added dropwise over 45 minutes. After the addition was complete, stirring was continued at 0° C. for 2.5 hours. The solution was transferred to a separatory funnel, diluted with CH$_2$Cl$_2$ (250 mL), washed with water, brine, dried over MgSO$_4$, and filtered. The solvent removed under reduced pressure to give the crude product as an oil. The crude product was purified by eluting (10% EtOAc/hexane) it through a short column of silica gel. The eluting solvent was removed in vacuo to leave a viscous oil of the titled intermediate. (78.1 g, 93 % overall yield). MS

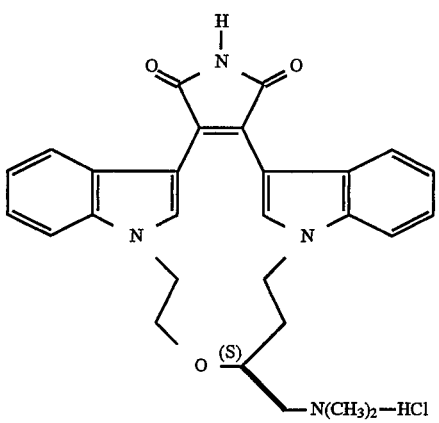

EXAMPLE 1 (326755)

(S)-13-[(dimethylamino)methyl]-10,11,14,15-tetrahydro-4,9:16-21-dimetheno-1H,13H-dibenzo[E,K]pyrrolo[3,4-H][1,4,13]oxadiazacyclohexadecine-1,3(2H)-dione 2,3-Bis-(1H-indol-3-yl)-N-methylmaleimide (114.7 g, 0.336 mole) and (S)-3-[2-[(methylsulfonyl)oxy]ethoxy]-4-(triphenylmethoxy)-1-butanol methane sulfonate (220.0 g, 0.401 mole, 1.2 eq.) were dissolved in 4.3 L of DMF. This solution of reagents was then added slowly over 70 hours (at approximately 1 mL/min) to a 50° C. slurry of cesium carbonate (437.8 g, 1.34 mole, 4.0 eq.) in 7 L of DMF. After 70–72 hours the reaction was cooled and filtered, and the DMF was removed in vacuo to give a residue that was dissolved in 4.6 L of $CH_2Cl_2$. The organic layer was extracted with 1.15 L of aqueous 1N HCl and then with 4.6 L of brine. The combined aqueous layers were back-extracted with 1.1 L of $CH_2Cl_2$. The combined organic layer was dried ($Na_2SO_4$) and filtered. Most of the solvent was removed in vacuo, and the resultant solution was filtered through 2 Kg of silica gel using 4–5 gallons of additional $CH_2Cl_2$ to remove baseline material. The solvent was removed in vacuo and the resultant purple colored solid triturated in 7 volumes of acetonitrile (based on weight of crude (S)-10,11,14,15-tetrahydro-2-methyl-13-[(triphenylmethoxy)methyl]-4,9:16,21-dimetheno-1H,13H-dibenzo[E,K]pyrrolo[3,4-H][1,4,13]oxadiazacyclohexadecine-1,3(2H)-dione to give 150.2 g (57%) of (S)-10,11,14,15-tetrahydro-2-methyl-13-[(triphenylmethoxy)methyl]-4,9:16,21-dimetheno-1H,13H-dibenzo[E,K]pyrrolo[3,4-H][1,4,131]oxadiazacyclohexadecine-1,3(2H)-dione after drying (89% pure by HPLC vs. standard).

(S)-10,11,14,15-tetrahydro-2-methyl-13-[(triphenylmethoxy)methyl]-4,9:16,21-dimetheno-1H,13H-dibenzo[E,K]pyrrolo[3,4-H][1,4,13]oxadiazacyclohexadecine-1,3(2H)-dione (32.7 g, 46.9 mmol) was suspended in 1.6 L of ethanol and 1.6 L of aqueous 10N KOH. The resultant mixture was heated to a gentle reflux (78° C.) for 19 hours. Most of the solids dissolved upon reaching reflux. The reaction solution was cooled to 10° to 15° C. and aqueous 10N HCl (1.2 L) was slowly added at <15° C. to adjust the acidity to pH=1. A red slurry developed upon acidification. The reaction mixture was diluted with 500 mL of $CH_2Cl_2$ and was stirred for 20 minutes and filtered to remove most of the salts. The salts were washed with additional $CH_2Cl_2$ (1.5 L), and the filtrate was extracted twice with 1 L of water. The combined aqueous layers were back-extracted with 1 L of $CH_2Cl_2$, and the organic layer was dried ($MgSO_4$). The solvent was removed in vacuo to give 36.0 g (>100%) (S)-10,11,14,15-tetrahydro-13-[(triphenylmethoxy)methyl]-4,9:16,21-dimetheno-13H-dibenzo[E,K]furo[3,4-H][1,4,13]oxadiazacyclohexadecine-1,3-dione as a purple solid (80% pure by HPLC area).

(S)-10,11,14,15-tetrahydro-13-[(triphenylmethoxy)methyl]-4,9:16,21-dimetheno-13H-dibenzo[E,K]furo[3,4-H][1,4,13]oxadiazacyclohexadecine-1,3-dione (36.0 g, assume 46.9 mmol) was dissolved in 320 mL of dry DMF under $N_2$ and was treated with a pre-mixed solution of 1,1,1,3,3,3-hexamethyldisilazane (99 mL, 75.7 g, 0.469 mol, 10 eq.) and methanol (9.5 mL, 7.51 g, 0.235 mol. 5 eq.). The resultant solution was heated at 45° C. for 7 hours. The reaction can be monitored by HPLC. Most of the DMF was removed in vacuo, and the resultant residue was extracted into 200 mL of ethyl acetate and washed with 200 mL of water and twice with 100 mL of an aqueous 5% LiCl solution. The aqueous layers were back-extracted with 100 mL of ethyl acetate. The combined organic layer was washed with 200 mL of a saturated aqueous solution of ammonium chloride. The combined organic layer was dried ($MgSO_4$) and evaporated in vacuo to give 35.9 g (>100%) of the crude (S)-10,11,14,15-tetrahydro-13-[(triphenylmethoxy)methyl]-4,9:16,21-dimetheno-1H; 13H-dibenzo[E,K]pyrrolo[3,4-H][1,4,13]oxadiazacyclohexadecine-1,3(2H)-dione as a purple solid. The 35.9 g of crude (S)-10,11,14,15-tetrahydro-13-[(triphenylmethoxy)methyl]-4,9:16,21-dimeth-eno-1H; 13H-dibenzo[E,K]pyrrolo[3,4-H][1,4,13]oxadiazacyclohexadecine-1,3(2H)-dione was dissolved in 350 mL of acetone, cesium fluoride (4.0 g, 26.3 mmol, 0.5 eq.) was added, and the resultant mixture was stirred for 1.5 hours to remove the N-silyl derivative of (S)-10,11,14,15-tetrahydro-13-[(triphenylmethoxy)methyl]-4,9:16,21-dimeth-eno-1H; 13H-dibenzo[E,K]pyrrolo[3,4-H][1,4,13]oxadiazacyclohexadecine-1,3(2H)-dione. The reaction mixture was filtered, and the cesium salts were washed with acetone. The solvent was removed in vacuo. The resultant residue (941 g) was diluted with 300 mL of ethyl acetate and was extracted with 150 mL of water with 25 mL of brine to improve layer separation. The organic layer was then washed with 150 mL more water and the combined organic layer was washed with 100 mL of brine, dried ($MgSO_4$) and was the solvent removed in vacuo to give 34.2 g (>100%) (S)-10,11,14,15-tetrahydro-13-[(triphenylmethoxy)methyl]-4,9:16,21-dimeth-eno-1H; 13H-dibenzo[E,K]pyrrolo[3,4-H][1,4,13]oxadiazacyclohexadecine-1,3(2H)-dione as a purple solid (90% pure by HPLC area).

(S)-10,11,14,15-tetrahydro-13-[(triphenylmethoxy)methyl]-4,9:16,21-dimeth-eno-1H; 13H-dibenzo[E,K]pyrrolo[3,4-H][1,4,13]oxadiazacyclohexadecine-1,3(2H)-dione (34.0, assume 46.8 mmol) was dissolved in 350 mL of $CH_2Cl_2$ and was cooled to −25° C. under $N_2$. Anhydrous HCl gas was bubbled into the reaction solution for approximately 1–2 minutes at <0° C. The resultant slurry was allowed to warm to room temperature and stir for 1 hour. The reaction can be monitored by HPLC. The slurry was filtered and the solids were washed with 200 mL of $CH_2Cl_2$. The solid was dried in a vacuum oven at 50° C. to give 18.6 g (90%) (S)-10,11,14,15-tetrahydro-13-(hydroxymethyl)-4,9:16,21-dimetheno-1H, 13H-dibenzo [E,K]pyrrolo [3,4-H][1,4,13 ]oxadiazacyclohexadecine-1,3 (2H)-dione as a purple solid (93% pure by HPLC area).

A suspension of (S)-10,11,14,15-tetrahydro-13-(hydroxymethyl)-4,9:16,21-dimetheno-1H,13H-dibenzo[E, K]pyrrolo[3,4-H][1,4,13]oxadiazacyclohexadecine-1,3(2H)-dione (18.2 g, 41.2 mmol) in 900 mL of THF was treated with pyridine (9.78 g, 10.0 mL, 0.124 mmol, 3 eq.) and methanesulfonic anhydride (14.3 g, 80.4 mmol, 2 eq.) and was heated to reflux (67° C.) for 16 hours under $N_2$. This reaction can be monitored by HPLC. The reaction was then cooled and diluted with 600 mL of ethyl acetate and extracted twice with 300 mL of 1N HCl and once with 600 mL of water. The aqueoues layers were back-extracted with 300 mL of ethyl acetate and the organic layer dried ($MgSO_4$). The solvent was removed in vacuo to give 19.0 of (S)-10,11,14,15-tetrahydro-13-[[methylsulfonyl)oxy] methyl]-4,9:16,21-dimetheno-1H,13H-dibenzo[[E,K]pyrrolo[3,4-H][1,4,13]oxadiazacyclohexadecine-1,3(2H)-dione that was triturated in 190 mL of hot (40° C.) $CH_2Cl_2$ and was filtered hot and washed with 100 mL of additional room temperature $CH_2Cl_2$ to give 17.3 g (81%) of (S)-10,11,14,15-tetrahydro-13-[[methylsulfonyl)oxy]methyl]-4,9:16,21-dimetheno-1H,13H-dibenzo[[E,K]pyrrolo[3,4-H][1,4,13]oxadiazacyclohexadecine-1,3(2H)-dione as a purple solid (96% pure by HPLC area).

(S)-10,11,14,15-tetrahydro-13-[[methylsulfonyl)oxy]methyl]-4,9:16,21-dimetheno-1H,13H-dibenzo[[E,K]pyrrolo[3,4-H][1,4,13]oxadiazacyclohexadecine-1,3(2H)-dione (9.50 g, 18.3 mmol) was dissolved in 475 mL of THF and 172 mL of a 40% aqueous solution of dimethylamine (0.173 mole, 75 eq.) was added, the resultant solution was heated at 65° C. in a sealed reactor (8–10 psi.) for 19 hours. The reaction was cooled and diluted with 900 mL of ethyl acetate and the organic layer was extracted twice with 450 mL of water and once with 200 mL of brine. The aqueous layers were back-extracted with 250 mL of additional ethyl acetate and the organic layer was dried ($MgSO_4$), and the solvent was removed in vacuo to give 7.82 g of (S)-13-[dimethylamino)methyl]-10,11,14,15-tetrahydro-4,9:16,21-dimetheno-1H,13H-dibenzo[E,K]pyrrolo[3,4- H][1,4,13]oxadiazacyclohexadecine-1,3(2H)-dione (91%).

(S)-13-[dimethylamino)methyl]-10,11,14,15-tetrahydro-4,9:16,21-dimetheno-1H,13H-dibenzo[E,K]pyrrolo[3,4-H][1,4,13]oxadiazacyclohexadecine-1,3(2H)-dione (3.0 g, 6.40 mmol) was suspended in 60 mL of type 3A ethanol and was cooled to –10° C. under $N_2$. Anhydrous HCl gas was bubbled into the reaction for approximately one minute at <10° C. and the resultant slurry allowed to warm and stir at room temperature for 2 hours. The slurry was filtered and the solid was washed with 30 mL of ethanol to give 3.04 g (94%) of (S)-13-[(dimethylamino)methyl]-10,11,14,15-tetrahydro-4,9:16–21-dimetheno-1H,13H-dibenzo[E,K]pyrrolo[3,4-H[]1, 4,13]oxadiazacyclohexadecine-1,3(2H)-dione monohydrochloride after drying.

$^1$H NMR: (d$_6$-DMSO) δ2.1 (m, 1H); 2.35 (m, 1H); 2.68 (s, 6H); 3.2 (m, 1H,); 3.33 (m, 1H); 3.66 (br. t, 1H); 3.8 (br. t, 1H); 3.85 (m, 1H); 4.17 (m, 1H); 4.2–4.4 (m, 3H); 7.1 (d, 1H); 7.13 (d, 1H); 7.2 (m, 2H); 7.44 (s, 1H); 7.48 (s, 1H); 7.5 (d, 1H); 7.56 (d, 1H); 7.82 (br.t, 2H); 10.59 (br., 1H); 10.96 (s, 1H).

EXAMPLE 2

(S)-3-[2-[(methylsulfonyl)oxy]ethoxy]-4-(triphenylmethoxy)-1-butanol methanesulfonate A 1M THF solution of vinylmagnesium bromide (5.76 L, 5.76 mole, 1.96 eq.) was cooled to –20° C. under $N_2$ and a catalytic amount of copper iodide was added (28.2 g, 0.148 mole, 0.05 eq.). The resultant mixture was stirred at –20° C. for 5 minutes, and then a solution of (S)-Trityl-glycidol (929.0 g, 2.94 mole) in 3.2 L of dry THF was added dropwise over 1.5 hours at –20° C. The reaction mixture was stirred for 1 hour at –20° C. The reaction was quenched by cooling the reaction mixture to –30° C. and 5 L of an aqueous saturated solution of ammonium chloride was slowly added. The organic layer was then extracted twice with 1 L a 10% wt./volume solution of ethylenediaminetetraacetic acid, disodium salt dihydrate (EDTA) to remove any metals. The organic layer was washed with 2 L of brine, dried ($MgSO_4$) and evaporated in vacuo to give 1061 g (96%) of (S)-1-(triphenylmethoxy)-4-penten-2-ol as an oil.

A 60% suspension of sodium hydride in mineral oil (268.9 g, 6.72 mole, 1.5 eq.) was suspended in 2.8 L of dry THF under $N_2$ and a solution (S)-1-(triphenylmethoxy)-4-penten-2-ol (1543 g, 4.48 mole) in 5.6 L of dry THF was added at room temperature. The resultant mixture was stirred at room temperature for 1.5 hours and then 770 mL (8.89 mole, 2.0 eq.) of freshly distilled allyl bromide was added over 20 minutes. The reaction was heated to 45° C. for 1–2 hours. The reaction mixture was cooled to 15°–20° C. and 2 L of an aqueous saturated solution of ammonium chloride was slowly added to quench the excess base. The resultant mixture was diluted with 1 L of ethyl acetate and 1 L of water and the organic layer was isolated. The aqueous layer was back-extracted with 500 mL of ethyl acetate and the combined organic layers were dried ($MgSO_4$) and evaporated in vacuo to give 1867 g (98%) of (S) -1,1',1"-[[[2-(2-propenyloxy) -4-pentenyl]oxy]methylidyne]tris [benzene] as a yellow oil.

(S)-1,1',1"-[[[2-(2-propenyloxy)-4-pentenyl]oxy]methylidyne]tris[benzene] (1281 g, 3.33 mole) was dissolved in a solution of 4 L of anhydrous methyl alcohol and 3.6 L of $CH_2Cl_2$ and was cooled to –50° to –40° C. while bubbling $N_2$ through the viscous reaction solution. Sudan III indicator was added to the reaction and ozone was bubbled through the reaction mixture at –50° to –35° C. for 13 hours until the reaction turned from a peach color to a light green/yellow color. The resultant reaction mixture was allowed to warm to 0° C. under $N_2$ and was then slowly added over 40 minutes to a solution of sodium borohydride (754 g, 19.9 mole, 6 eq.) in 2.5 L ethanol/2.5 L water while keeping the reaction temperature below 30° C. The reaction was then allowed to stir at room temperature overnight. The reaction can be monitored by HPLC. The reaction mixture was cooled to 10°–15° C. and was slowly added to 4 L of an aqueous saturated solution of ammonium chloride at <20° C. The quenched reaction mixture was then filtered and the solids washed with 3 L of $CH_2Cl_2$. The organic layer was isolated and was washed with 3 L of an aqueous saturated solution of ammonium chloride and the aqueous layers were back-extracted with 1 L of $CH_2Cl_2$. The combined organic layer was dried ($MgSO_4$) and evaporated in vacuo to give a 1361 g (>100%) of (S)-3-(2-hydroxyethoxy)-4-(triphenylmethoxy)-1-butanol as a oil.

(S)-3-(2-hydroxyethoxy)-4-(tripenylmethoxy)-1-butanol (500 g, 1.27 mole) was dissolved in 4.8 L of $CH_2Cl_2$, was cooled to 0° C. under $N_2$, and triethylamine (386.4 g, 532 mL, 3.81 mole, 3.0 eq.) was added. Methanesulfonyl chloride (396.3 g, 268 mL, 3.46 mole, 2.7 eq.) was then added dropwise over 30 minutes at <5° C. The resultant reaction mixture was stirred at 0° to 5° C. for 1–2 hours and was monitored by HPLC. The reaction mixture was diluted with additional $CH_2Cl_2$ and was washed twice with 2 L of water and 2 L of an aqueous saturated solution of ammonium chloride. The aqueous layers were back-extracted with 1 L of $CH_2Cl_2$ and the combined organic layer was dried ($MgSO_4$) and evaporated in vacuo to give a crude solid that was recrystallized from 1/1 heptane/ethyl acetate to give 615 g (88%) of (S)-3-[2-[(methylsulfonyl)oxy]ethoxy]-4-(triphenylmethoxy)-1-butanol methane sulfonate in three crops as a solid. NMR. MS.

EXAMPLE 3

D-[2-iodoethoxy]-4-(tripenylmethoxy-iodobutone

Trityl chloride (175.2 g, 0.616 mole) was dissolved in 500 mL of $CH_2Cl_2$ under $N_2$. Triethylamine (71.9 g, 100 mL, 0.710 mole) was added and then R,S-glycidol (50.0 g, 0.648 mole) was added, and the reaction solution was heated to a gentle reflux (42° C.) for 4 hours. The reaction was cooled to room temperature and was extracted twice with 250 mL of an aqueous saturated solution of ammonium chloride and then 250 mL of brine. The aqueous layers were back-extracted with 100 mL of $CH_2Cl_2$ and the organic layer was dried ($MgSO_4$) and evaporated in vacuo to give trityl-glycidol as an oil that was recrystallized from ethanol to give 104.4 g (54%) of trityl-glycidol as a solid.

A 1M THF solution of vinylmagnesium bromide (50 mL, 50 mmol, 2.0 eq.) was cooled to -20° C. under $N_2$ and a catalytic amount of copper iodide was added (0.24 g, 1.26 mmol, 0.05 eq.). The resultant mixture was stirred at -20° C. for 5 minutes and then a solution of trityl-glycidol (7.91 g, 25.0 mmol) in 40 mL of dry THF was added dropwise over 15 minutes at -20° C. The reaction mixture was stirred for 3 hours at -20° C. and then was allowed to warm to room temperature and stir for 15 minutes. The reaction was quenched by cooling the reaction mixture to -30° C. and 125 mL of an aqueous saturated solution of ammonium chloride was slowly added. The resultant mixture was extracted with 200 mL of ethyl acetate. The organic layer was then extracted with an aqueous solution of 0.93 g (2.50 mmol, 0.1 eq.) of ethylenediaminetetraacetic acid, disodium salt dihydrate (EDTA) in 125 mL of deionized water to remove any metals. The aqueous layers were back extracted with 50 mL of ethyl acetate and the combined organic layers were washed with 100 mL of brine, dried ($MgSO_4$) and evaporated in vacuo to give an oil that was filtered through silica (76 g) using 1.2 L of 3/1 hexanes/ethyl acetate. The filtrate was evaporated in vacuo to give 9.07 g of 1-(triphenylmethoxy)-4-penten-2-ol as a light yellow colored oil (100%).

A 60% suspension of sodium hydride in mineral oil (6.13 g, 0.153 mol, 1.5 eq.) was suspended in 175 mL of dry THF was added at room temperature. The resultant mixture was stirred at room temperature for 1.5 hours and then 17.7 mL (0.204 mmol, 2.0 eq.) of freshly distilled allyl bromide was added via syringe. The reaction was heated to 45° C. for 1 hour. The reaction can be monitored by TLC or HPLC. The reaction mixture was cooled to 0° C. and 400 mL of an aqueous saturated solution of ammonium chloride was slowly added to quench the excess base. The resultant mixture was extracted with 800 mL of ethyl acetate and the organic layer was washed with 500 mL of water. The aqueous layers were back-extracted with 100 mL of ethyl acetate and the combined organic layers were washed with 200 mL of brine, dried ($MgSO_4$) and evaporated in vacuo to give 41.5 g (>100%) of 1,1',1"-[[[2-(2-propenyloxy)-4-pentenyl]oxy]methylidyne]tris[benzene]as a yellow oil.

1,1',1"-[[[2-(2-propenyloxy)-4-pentenyl]oxy]methylidyne]tris[benzene](39.3 g, 0.102 mol) was dissolved in a solution of 390 mL of anhydrous methyl alcohol and 60 mL of $CH_2Cl_2$ and was cooled to -50° to -40° C. while bubbling $N_2$ through the viscous reaction solution. Ozone was then bubbled through the reaction mixture at -50° to -40° C. for 80 minutes until the reaction turned pail blue in color. The resultant reaction mixture was allowed to warm to 0° C. under $N_2$ and then a solution of sodium borohydride (23.15 g, 0.612 mole, 6 eq.) in 85 mL ethanol/85 mL water was slowly added to quench the reaction while keeping the reaction temperature below 10° C. The reaction was stirred in an ice bath for 30 minutes and then was allowed to warm to room temperature and stir overnight. The temperature rose to 31° C. upon warming. The reaction mixture was diluted with 400 mL of an aqueous saturated solution of ammonium chloride and was extracted with 800 mL of ethyl acetate. The organic layer was washed with 400 mL of water and the aqueous layers were back-extracted with 150 mL of ethyl acetate. The combined organic layer was washed with 200 mL of brine and was dried ($MgSO_4$) and evaporated in vacuo to give a cloudy oil. This oil was recrystallized from 2/1 hexanes/ethyl acetate in 3 crops to give 28.9 g of 3-(2-hydroxyethoxy)-4-(triphenylmethoxy)-1-butanol (72%).

3-(2-hydroxyethoxy)-4-(triphenylmethoxy)-1-butonol (14.0 g, 35.7 mmol) was dissolved in 140 mL of $CH_2Cl_2$, was cooled to 0° C. under $N_2$, and triethylamine (10.8 g, 14.9 mL, 0,107 mol. 3.0 eq.) was added. Methanesulfonyl chloride (11.0 g, 7.46 mL, 96.4 mmol, 2.7 eq.) was then added dropwise at <5° C. The resultant reaction mixture was diluted with additional $CH_2Cl_2$ (300 mL) and was washed with 200 mL of water and 200 mL of an aqueous saturated solution of ammonium chloride. The aqueous layers were back-extracted with 50 mL of $CH_2Cl_2$ and the combined organic layer was washed with 100 mL of brine and was dried ($MgSO_4$) and evaporated in vacuo to give 18.4 g (94%) of 3-(2-[(methylsulfonyl)oxy]ethoxy]-4-triphenylmethoxy)-1-butanol methane sulfonate as a white solid.

A solution of 3-(2-[(methylsulfonyl)oxy]ethoxy]-4-triphenylmethoxy)-1-butanol methane sulfonate (5.0 g, 9.10 mmol) in 500 mL of reagent grade acetone was treated with sodium bicarbonate (0.0770 g, 0910 mmol, 0.1 eq.) and sodium iodide (34.2 g, 0.228 mol. 25 eq.). The resultant mixture was stirred at 50° C. under $N_2$ for approximately 16 hours. This reaction can be monitored by HPLC. The acetone was removed from the reaction mixture in vacuo and the resultant solid was extracted into a 300 mL of ethyl acetate/200 mL water mixture. The organic layer was washed with 200 mL more water and the combined aqueous layer was back-extracted with 100 mL of additional ethyl acetate. The combined organic layer was washed with 200 mL of a 10% aqueous solution of sodium sulfite (this wash removed the yellow color), 100 mL of brine, was dried ($MgSO_4$), and was evaporated in vacuo to give 5.45 g (98%) of 3-[2-iodoethoxy]-4-(tripenylmethoxy-iodobutane as a clear oil. MS. NMR.

EXAMPLE 4

1-(tert-butyldimethylsilyloxy)-2-(3-iodopropyloxy)-4-(tert-butyldiphenylsilyloxy)-butane To a methylene chloride (20 mL)/cyclohexane (100 mL) solution of the alcohol of Preparation 4 was added allyl trichloroacetimidate (17.82 g, 88 mmols, 2.2 eq) under an $N_2$ balloon followed by trifluoromethanesulfonic acid (50 µL/g of starting material, 0.92 mL). After 20 hours, the solution was filtered, and the filtrate was washed with saturated aqueous $NaHCO_3$, water, and then brine. The organic layer was collected and dried over $MgSO_4$. The solvent was removed to give an oil, which was purified by flash chromatography on silica gel eluting with hexanes and increasing the polarity of the mobile phase to 5% ethyl acetate in hexanes over several liters to Yield 19.27 g of the alkyl ether as a light brown oil (97% yield). MS.

To a THF (60 mL) solution of the above allyl ether (14.16 g, 28.38 mmols, 1 eq) was added 9-BBN (9-borabicyclo [3.3.1]nonane, 0.5M solution in THF, 60 mL, 30 mmols, 1.1 eq) dropwise under nitrogen. After 3 hours, TLC (10% EtOAc in hexanes) of the reaction showed that the starting material had been consumed. To this solution was added 3M aqueous NaOH (10.41 mL, 31.22 mmols, 1.1 eq) followed by slow (1.5 hr) dropwise addition of 30% hydrogen peroxide (10.3 mL, 90.82 mmols, 3.2 eq). The reaction temperature during the peroxide quench was kept below 50 °C. (ice bath).

After 30 minutes, sodium chloride was added until the solution was saturated. The organic layer was removed; the aqueous layer was extracted with ether; the combined organic layers were dried and filtered; and the filtrate concentrated to give an oil. The crude oil was purified by flash chromatography on silica gel eluting with 10% EtOAc/hexanes and increasing the polarity to 20% EtOAc/hexanes after about 1.5 liters of Solvent to yield 9.53 g of a light yellow oil (65% yield). MS.

To an anhydrous 0° C. ether (150 mL) solution of the above alcohol was added triethylamine (2.93 g, 28.91 mmols, 1.5 eq.) followed by dropwise addition of mesyl chloride (3.31 g, 28.91 mmols, 1.5 eq.) with vigorous stirring. After 3 hours at 0° C., TLC (10% EtOAc in hexanes) indicated the starting material was consumed. The reaction was diluted with ether, washed with water, brine, dried over MgSO₄, and the solvent removed. The resulting oil was passed through a pad of silica eluting with 25% EtOAc/hexanes, and the eluant was concentrated. To an acetone (200 mL) solution of the resulting oil was added NaHCO₃ (0.17 g, 1.93 mmols, 0.1 eq.), and NaI (28.88 g, 192.7 mmols, 10 eq.). After stirring 30 minutes at room temperature under a nitrogen atmosphere, the reaction was heated to 50 °C. with a water bath. After 2.5 hours, TLC (10% EtOAc in hexanes) indicated that the mesylate was consumed. The reaction mixture was diluted with ether (500 mL), washed with cold saturated aqueous Na₂SO₃, water, brine, dried (MgSO₄), and the solvent removed. The resulting oil was passed through a pad of silica eluting with 5% EtOAc in hexanes to give the purified titled compound 10.3 g as a colorless oil (85% yield).

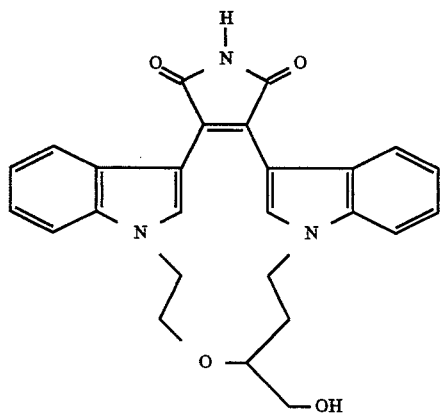

EXAMPLE 5

3,4-[(N,N'-1,1'-((2'ethoxy)-3'(O)-4'''-(hydroxy)-butane)-bis-(3,3'-indolyl)]-1(H)-pyrrole-2,5-dione (320283)

To a dimethylformamide (250 mL) solution of bis-(3,3'-indolyl)-1-(methyl)-pyrrole-2,5-dione 301129(17.9 g, 52.5 mmol, 3 eq) under nitrogen was added cesium carbonate (68.4 g, 4 eq). To the resulting suspension was added the iodide, 1-(tert-butyldimethylsilyloxy)-3-(2-iodoethoxy)-4-(tert-butyldiphenylsilyloxy)-butane, (10.7 g, 17.5 mmol). The reaction stirred for 18 hours at room temperature. TLC (5% ethyl acetate/hexane) showed disappearance of the iodide. The reaction was poured into ethyl acetate (1200 mL) and washed with 1N HCl (400 mL) followed by backwash with ethyl acetate (2×). The combined ethyl acetate portions were washed with saturated sodium bicarbonate solution, brine (2×), dried (MgSO₄), filtered and concentrated down in vacuo. Dimethylformate was removed by azeotroping with xylene. The resulting red gum was slurried in dichloromethane and acetonitrile to give a solid suspension. It was concentrated down, more dichloromethane added, cooled and filtered to give a red solid. Some of the desired product was extracted from this solid by another trituration in dichloromethane and then in ethyl acetate. The filtrates were concentrated in vacuo and the resulting residue absorbed on silica and applied to a large flash column. Dialkylated by-product was removed by elution with 5 hexane/1 ethyl acetate followed by elution of the product with 3 hexane/1 ethyl acetate to provide 8.2 g (57%) of the monoalkylated product, 3-[(N-1-(2-ethoxy-(3'''-(O) 4'''-(tert-butyldiphenylsilyloxy)-1'''(tert-butyldimethylsilyloxy)-butane))-indol-3-yl]-4-[indol-3-yl]-1N(methyl)-pyrrole-2,5-dione.

To a methanol (450 mL) solution of the tert-butyldimethylsilyl ether, 3-[(N-1-(2-ethoxy-(3'''-(O)-4'''-(tert-butyldiphenylsilyloxy)-1'''-(tert-butyldimethylsilyloxy)-butane))-indol-3-yl]-4-[indol-3-yl]-1N(methyl)-pyrrole-2,5-dione (8.2 g, 9.9 mmol) under nitrogen at 5 °C. was added p-toluenesulfonic acid, monohydrate (0.16 g, 0.085 eq). After 2 hours, TLC (50% ethyl acetate/hexane) showed the reaction to be nearly complete. The reaction was quenched with solid sodium bicarbonate (0.14 g). The methanol was removed in vacuo. The resulting residue was dissolved in ethyl acetate, washed with 0.1N sodium hydroxide, brine (2×), dried (MgSO₄), filtered and concentrated in vacuo to give a red foam. This material was absorbed on silica and placed on a silica pad. Elution with 2 hexane/1 ethyl acetate removed residual starting material followed by elution with 1 hexane/1 ethyl acetate and 1 hexane/2 ethyl acetate to provide 6.4 g(91%) of the alcohol, 3-[(N-1-(2-ethoxy-(3'''-(O)-4'''-(tert-butyldiphenylsilyloxy)-1'''-(hydroxy)-butane))-indol-3-yl]-4-[indol-3-yl]-1N (methyl)-pyrrole-2,5-dione.

To an anhydrous ether (500 mL) solution of the alcohol, 3-[(N-1-(2-ethoxy-(3'''-(O)-4'''-(tert-butyldiphenylsilyloxy)-1'''-(hydroxy)-butane))-indol-3-yl]-4-[indol-3-yl]-1N (methyl)-pyrrole-2,5-dione (6.36 g, 8.9 mmol) under nitrogen at 5° C. was added triethylamine (1.9 mL, 1.5 eq) and methanesulfonyl chloride (1.0 mL, 1.5 eq). After 3 hours, additional triethylamine (1.25 mL, 1.0 eq) and methanesulfonyl chloride (0.7 mL, 1.0 eq) were added. After 1 hour, the reaction was shown to be complete by TLC (50% ethyl acetate/hexane). The reaction was diluted with ether (250 mL), washed with water, 0.1N HCl and brine (2×). The ether was dried (MgSO₄), filtered, and concentrated in vacuo to provide 7.0 g of mesylate, 3-[(N-1-(2-ethoxy-(3'''-(O)-4'''-(tert-butyldiphenylsilyloxy)-1'''-(methanesulfonyloxy)-butane))indol-3-yl]-4-[indol-3-yl]-1N(methyl)-pyrrole-2,5-dione.

To an acetone (200 mL) solution of the mesylate, 3-[(N-1-(2-ethoxy-(3'''-(O)-4'''-(tert-butyldiphenylsilyloxy)-1'''-(methanesulfonyloxy)-butane))-indol-3-yl]-4-[indol-3-yl]-1N(methyl)-pyrrole-2,5-dione, (7.0 g, 8.9 mmol) under nitrogen was added sodium iodide (13.3 g, 10 eq) and sodium bicarbonate (75 mg, 0.1 eq). The mixture was stirred at 50° C. for 13 hours. The reaction was concentrated in vacuo, and the residue was dissolved in ether and washed with 10% sodium sulfite solution. The layers were separated, and the ether portion washed with 10% sodium sulfite solution, water, brine(2×), dried, and concentrated in vacuo. The residue was passed through a silica pad by eluting with 1 hexane/1 ethyl acetate and 1 hexane/2 ethyl acetate to provide 7.6 g of the iodide, 3-[(N-1-(2-ethoxy-(3'''-(O)-4'''-(tert-butyldiphenylsilyloxy)-1'''-(iodo)-butane))-indol-3-yl]-4-[indol-3-yl]-1N(methyl)-pyrrole-2,5-dione as a red solid (quantitative yield for the two steps).

To a dimethylformamide (1 L) suspension of cesium carbonate (12.0 g, 4 eq) under nitrogen was added the iodide, 3-[(N-1-(2-ethoxy-(3'''-(O)-4'''-(tert-butyldiphenylsilyloxy)-1'''-(iodo)-butane))-indol-3-yl]-4-[indol-3-yl]-1N(methyl)-pyrrole-2,5-dione (7.6 g, 9.2 mmol), dissolved in dimethylformamide(25 mL) via syringe pump over 65 hours. Three hours after the addition was complete, the reaction was concentrated in vacuo. The residue was dissolved in ethyl acetate (700 mL), washed with water (2×300 mL), and the aqueous layer backwashed with ethyl acetate (2×200 mL). The combined ethyl acetate portions were washed with brine (2×200 mL), dried (MgSO$_4$), filtered and concentrated in vacuo to provide a purple residue. The material was absorbed onto silica and applied to a flash column. Eluted with 3 hexane/1 ethyl acetate and then 1hexane/1 ethyl acetate to give 5.2 g(82%) of the macrocycle, 3,4-[(N,N'-1,1'-((2''-ethoxy)-3'''(O)-4'''-(tert-butyldiphenylsilyloxy)-butane)-bis-(3,3'-indolyl)]-1(H)--pyrrole-2,5-dione.

A suspension of the N-methyl maleimide, 3,4-[(N,N'-1,1'-((2''-ethoxy)-3'''(O)-4'''-(tert-butyldiphenylsilyloxy)-butane)-bis-(3,3'-indolyl)]-1(H)-pyrrole-2,5-dione in 5N KOH (150 mL) and ethanol (300 mL) was stirred at room temperature for 65 hours and then for one hour at 60° C. The reaction was concentrated (150 mL) in vacuo, the residue suspended in water, cooled to 5° C., and acidified (pH 3) with concentrated hydrochloric acid. The red aqueous suspension was extracted with ethyl acetate (4×200 mL), dried, and concentrated in vacuo to give 3.3 g of the crude anhydride alcohol, 2,3-[(N,N'-1,1'-((2''-ethoxy)-3'''(O)-4'''-(hydroxy)-butane)-bis-(3,3'-indolyl)]-furan-1,4-dione as a purple solid.

To a dimethylformamide (250 mL) solution of the anhydride,2,3-[(N,N'-1,1'-((2''-ethoxy)-3'''(O)-4'''-hydroxy)-butane)-bis-(3,3'-indolyl)]-furan-1,4-dione, (3.3 g, 7.5 mmol) under nitrogen was added 1,1,1,3,3,3-hexamethyldisilazane (32 mL, 2 eq) and methanol (3 mL, 10 eq). The reaction was stirred at room temperature for 16 hours and then heated at 60° C. for 2 hours. The dimethylformamide was removed in vacuo, and the resulting residue was dissolved in acetonitrile (250 mL). 1N HCl (50 mL) was added. The reaction was stirred for 15 minutes. The reaction was concentrated, partitioned between ethyl acetate (1 L) and water (250 mL). The product was a solid that precipitated giving the alcohol maleimide, 3,4-[(N,N'-1,1'-((2'-ethoxy)-3'''(O)-4'''-(hydroxy)-butane)-bis-(3,3'-indolyl)]-1(H)-pyrrole-2,5-dione, 0.92(28%) of product. A small amount (50 mg) was absorbed on silica and applied to a flash column. Eluted with dichloromethane, 5% acetonitrile/dichloromethane and then 10% acetonitrile/dichloromethane to give 38 mg of analytically pure material. The ethyl acetate was concentrated and chromatographed to give an additional 8% of the crude product. MS.

$^1$H NMR (d$_6$-DMSO): δ1.96 (1H, m); 2.09 (1H, m); 3.31 (1H, m); 3.40 (1H, m); 3.51 (1H, m); 3.62 (1H, m); 3.89 (1H, m); 4.18 (3H, m); 4.35 (1H, m), 4.68 (1H, t, J=2 Hz); 7.11 (2H, m); 7.19 (2H, m); 7.44 (1H, s) 7.46 (1H, d, J=9 Hz); 7.51 (1H, s) 7.53 (1H, d, J=9 Hz); 7.79 (1H, d, J=8 Hz); 7.83 (1H, d, J=8 Hz); 10.91 (1H, s).

We claim:
1. A process which comprises
(a) Alkylating a compound of Formula (III):

wherein,
R$^2$ is —O-triphenylmethyl or —O-methoxytriphenylmethyl; Z is —(CH$_2$)$_n$—; and n is independently 1, 2, or 3 with a lithium acetylide, a cerium acetylide, or organometalic reagent selected from vinyl cuprate, vinyl aluminum, vinyl tin, vinyl lithium, or vinyl Grignard; to produce a compound of the Formula (IV):

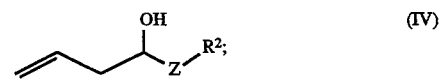

(b) Reacting a compound of the Formula (IV) with a compound of the Formula:

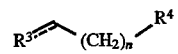

wherein R$^3$ is halo, a protected hydroxy, or combines with the adjacent carbon to form an olefin; R$^4$ is chloro, bromo, or iodo; and n is independently 1,2, or 3; to form a compound of the Formula (V):

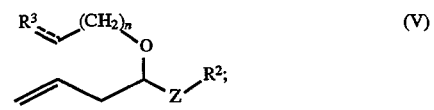

(c) Converting the compound of the Formula (V) to a compound of the Formula (II):

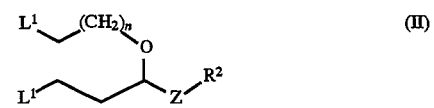

wherein:
L$^1$ is independently a leaving group; and
(d) Alkylating a compound of Formula (VIII):

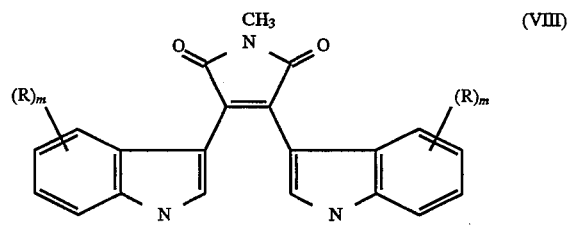

wherein R is independently hydrogen, halo, C$_1$-C$_4$ alkyl, hydroxy, C$_1$-C$_4$ alkoxy, haloalkyl, nitro, NR$^5$R$^6$, or —NHCO(C$_1$-C$_4$ alkyl), R$^5$ and R$^6$ are independently hydrogen, metal, phenyl, benzyl, or combine to the nitrogen to which they are bonded to form a saturated or unsaturated 5 or 6 membered ring, and m is independently 0, 1, 2, or 3, with a compound of Formula II, to produce a compound of the formula:

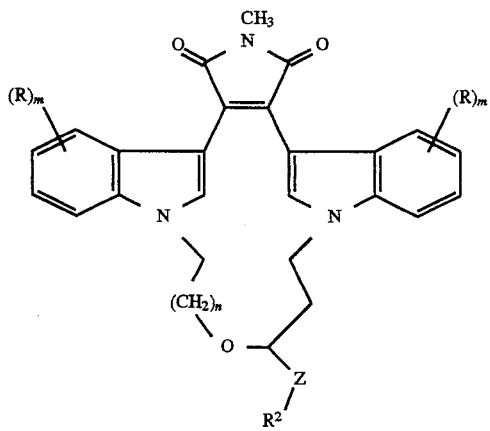

2. The process of claim 1 wherein the compound of Formula (VIII) is alkylated with a compound of Formula II in the presence of about 0.5 to about 10 equivalents of $Cs_2CO_3$.

3. A process which comprises

Alkylating a compound of Formula (IIIs):

(IIIs)

wherein,
$R^2$ is —O-triphenylmethyl or —O-methoxytriphenylmethyl; Z is —$(CH_2)_n$—; and n is independently 1, 2, or 3 with a lithium acetylide, a cerium acetylide, or organometalic reagent selected from vinyl cuprate, vinyl aluminum, vinyl tin, vinyl lithium, or vinyl Grignard; to produce a compound of the Formula (IVs):

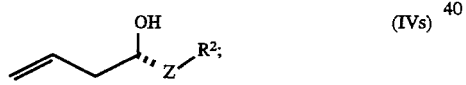
(IVs)

(b) Reacting a compound of the Formula (IVs) with a compound of the Formula:

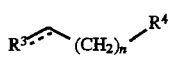

wherein $R^3$ is halo, a protected hydroxy, or combines with the adjacent carbon to form an olefin; $R^4$ is chloro, bromo, or iodo; and n is independently 1,2, or 3; to form a compound of the Formula (Vs):

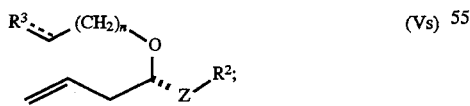
(Vs)

(c) Converting the compound of the Formula (Vs) to a compound of the Formula (IIs):

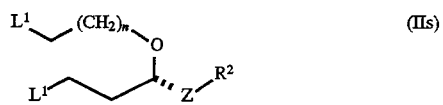
(IIs)

wherein $L^1$ is independently a leaving group; and (d) Alkylating a compound of Formula (VIII):

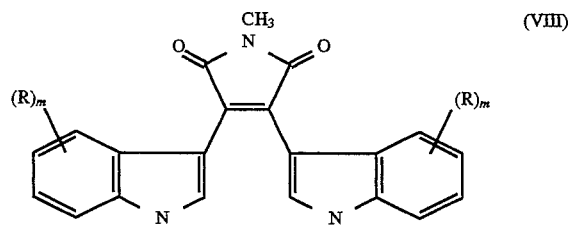
(VIII)

wherein R is independently hydrogen, halo, $C_1$–$C_4$ alkyl, hydroxy, $C_1$–$C_4$ alkoxy, haloalkyl, nitro, $NR^5R^6$, or —$NHCO(C_1$–$C_4$ alkyl); $R^5$ and $R^6$ are independently hydrogen, methyl, phenyl, benzyl, or combine to the nitrogen to which they are bonded to form a saturated or unsaturated 5 or 6 membered ring; m is independently 0, 1, 2, or 3; with a compound of Formula IIs, to produce a compound of the formula:

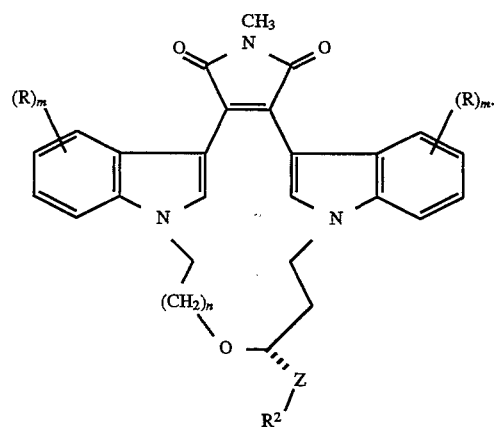

4. The process of claim 3 wherein the compound of Formula (VIII) is alkylated with a compound of Formula IIs in the presence of about 0.5 to about 10 equivalents of $Cs_2CO_3$.

5. A process which comprises (a) Alkylating a compound of Formula (IIIr):

(IIIr)

wherein $R^2$ is —O-triphenylmethyl or —O-methoxytriphenylmethyl; Z is —$(CH_2)_n$—; and n is independently 1, 2, or 3 with a lithium acetylide, a cerium acetylide, or organometalic reagent selected from vinyl cuprate, vinyl aluminum, vinyl tin, vinyl lithium, or vinyl Grignard; to produce a compound of the Formula (IVr):

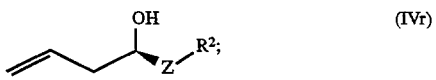
(IVr)

(b) Reacting a compound of the Formula (IVr) with a compound of the Formula:

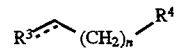

wherein $R^3$ is halo, a protected hydroxy, or combines with the adjacent carbon to form an olefin; $R^4$ is chloro, bromo, or iodo; and n is independently 1,2, or 3; to form a compound of the Formula (Vr)

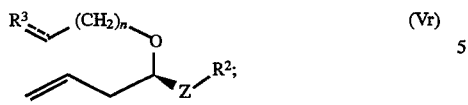

(c) Converting the compound of the Formula (Vr) to a compound of the Formula (IIr):

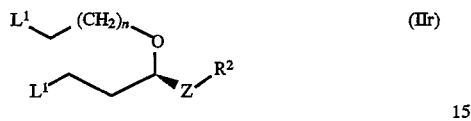

wherein $L^1$ is independently a leaving group; and (d) Alkylating a compound of Formula (VIII):

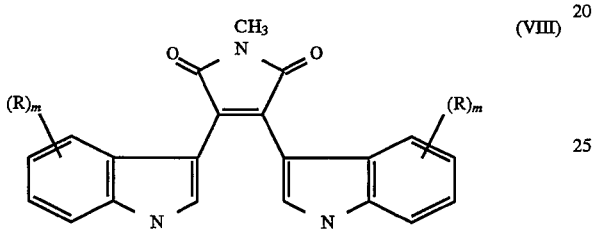

wherein R is independently hydrogen, halo, $C_1$–$C_4$ alkyl, hydroxy, $C_1$–$C_4$ alkoxy, haloalkyl, nitro, $NR^5R^6$, or —NHCO($C_1$–$C_4$ alkyl); $R^5$ and $R^6$ are independently hydrogen, methyl, phenyl, benzyl, or combine to the nitrogen to which they are bonded to form a saturated or unsaturated 5 or 6 membered ring; m is independently 0, 1, 2, or 3; with a compound of Formula IIr, to produce a compound of the formula:

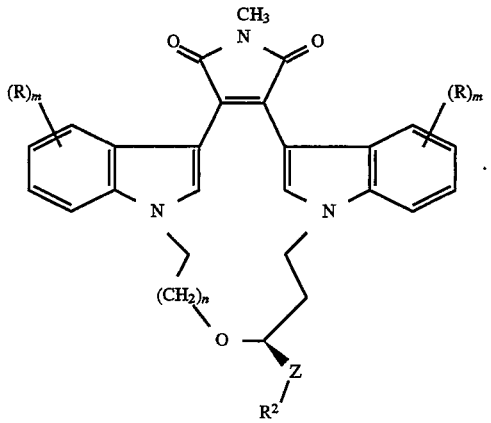

6. The process of claim 5 wherein the compound of Formula (VIII) is alkylated with a compound of Formula IIr in the presence of about 0.5 to about 10 equivalents of $Cs_2CO_3$.

* * * * *

UNITED STATES PATENT AND TRADEMARK OFFICE
CERTIFICATE OF CORRECTION

PATENT NO. : 5,665,877
DATED : September 9, 1997
INVENTOR(S) : Faul, et al.

It is certified that error appears in the above-identified patent and that said Letters Patent is hereby corrected as shown below:

Column 4, line 17, "trillate," should read --triflate,--.
Column 4, line 33, "(trityl," should read --(trityl),--.
Column 15, line 8, "D-[2-iodoethoxy]-4-(tripenylmethoxy-iodobutone" should read --3-[2-iodoethoxy]-4-(tripenylmethoxy-iodobutone--.
Column 16, line 21, "3-(2-hydroxyethoxy)-4-(triphenylmethoxy)-1-butonol" should read --3-(2-hydroxyethoxy)-4-(triphenylmethoxy)-1-butanol--.
Column 16, line 52, "3-[2-iodoethoxy]-4-(tripenylmethoxy-iodobutane" should read --3-[2-iodoethoxy]-4-(triphenylmethoxy-iodobutane--.
Column 17, line 4, "alkyl" should read --allyl--.
Column 17, line 63, "3,4-[(N,N'-1,1'-((2'ethoxy)-3'(0)-4'"-(hydroxy)-" should read --3,4-[(N,N' -1,1' -( (2" -ethoxy) -3'"(O)-4'" -(hydroxy) --
Column 18, line 25, "4'"-(tert-butyldiphenylsilyloxy)-1'"(tert-" should read --4'"-(tert-butyldiphenylsilyloxy)-1'"-(tert-"--.
Column 18, line 62, "butane))indol-3-yl]-4-[indol-3-yl]-1N(methyl)-pyrrole-2,5-" should read --butane))-indol-3-yl]-4-[indol-3-yl]-1N(methyl)-pyrrole-2,5---.

Signed and Sealed this

Seventeenth Day of November, 1998

Attest:

BRUCE LEHMAN

Attesting Officer

Commissioner of Patents and Trademarks